United States Patent [19]
Kitajima et al.

[11] Patent Number: 5,979,669
[45] Date of Patent: Nov. 9, 1999

[54] BLOOD FILTER UNIT

[75] Inventors: Masao Kitajima; Kenichiro Yazawa; Shigeru Tezuka, all of Saitama; Fumio Sugaya, Kanagawa; Akemi Higo; Kiyotaka Fujiwara, both of Saitama, all of Japan

[73] Assignee: Fuji Photo Film Co., Ltd., Kanagawa, Japan

[21] Appl. No.: 08/784,481

[22] Filed: Jan. 17, 1997

[30] Foreign Application Priority Data

Jan. 19, 1996 [JP] Japan .................................. 8-007692

[51] Int. Cl.⁶ .......................... B01D 29/05; B01D 29/56; B01D 29/92
[52] U.S. Cl. .......................... 210/455; 210/247; 210/477; 210/483; 210/488; 210/489; 210/503; 422/101
[58] Field of Search ..................... 210/455, 477, 210/483, 488, 489, 496, 503, 247; 422/101

[56] References Cited

U.S. PATENT DOCUMENTS

| | | | |
|---|---|---|---|
| 3,663,374 | 5/1972 | Moyer et al. | |
| 4,631,050 | 12/1986 | Reed et al. | 604/4 |
| 4,902,481 | 2/1990 | Clark et al. | 422/101 |
| 5,223,133 | 6/1993 | Clark et al. | 210/406 |
| 5,423,989 | 6/1995 | Allen et al. | 210/490 |
| 5,460,777 | 10/1995 | Kitajima et al. | 422/56 |
| 5,589,399 | 12/1996 | Allen et al. | 422/101 |
| 5,603,900 | 2/1997 | Clark et al. | 422/101 |

Primary Examiner—John Kim
Attorney, Agent, or Firm—McAulay Nissen Goldberg Kiel & Hand, LLP

[57] ABSTRACT

A blood filter unit having a blood filter holder containing a blood filtering material of a glass fiber filter and a microporous membrane is described. The holder has a blood inlet and a filtrate outlet, and accommodates the blood filtering material so that the microporous membrane is located on the filtrate outlet side and has a space between the blood filtering material and the filtrate outlet. The holder provides means for preventing adhesion of the blood filtering material on the filtrate outlet side. The inventive blood filter unit allows separation of a desired volume of plasma or serum for analysis without interference by the hematocrit value of the blood.

8 Claims, 13 Drawing Sheets

BLOOD FILTER UNIT

BACKGROUND OF THE INVENTION

This invention relates to a blood filter unite used for the preparation of plasma or serum sample from whole blood.

Type or concentration of blood components, such as metabolites, proteins, lipids, electrolytes, enzymes, antigens, and antibodies, is measured, in general, using a plasma or serum sample obtained by centrifuging whole blood. However, centrifuging takes labor and time. Particularly, centrifuging is unsuitable for an urgent case of measuring a small number of samples promptly and in site inspection, because of requiring a centrifuge and electricity. Thereupon, it has been investigated to separate serum from whole blood by filtration.

Several filtration methods using glass fiber filter have been known wherein whole blood is charged into the glass fiber in a column from one side of the column, and pressurized or sucked to obtain plasma or serum from the other side (Japanese Patent KOKOXU Nos. 44-14673, 5-52463, Japanese Patent KOKAI Nos 2-208565, 4-208856).

However, practical filtration methods capable of obtaining an amount of plasma or serum from whole blood necessary for measuring by an automatic analyzer have not been developed except a part of items, such as blood sugar.

Moreover, dispersion of hematocrit values is great, and according to the kind of blood, a necessary amount of plasma could not been obtained by clogging filtering material or breakthrough of blood cells.

SUMMARY OF THE INVENTION

An object of the invention is to provide a blood filter unit capable of separating plasma or serum efficiently even from a very small amount of blood without breakthrough and hemolysis.

Another object of the invention is to provide a blood filter unit capable of separating plasma or serum stably from blood, irrespective of hematocrit value.

The inventors investigated eagerly in order to solve the aforementioned problems, and found that it is effective to use a combination of glass fiber filter and microporous membrane as blood filtering material and to provide a means for preventing adhesion of the blood filtering material on the filtrate outlet side.

They also found that it is effective to incorporate a flow area-regulating member which regulates outflow of filtrate.

Thus, the present invention provides a blood filter unit which comprises a blood filtering material comprising glass fiber filter and microporous membrane, and a holder having a blood inlet and a filtrate outlet, accommodating the blood filtering material so that the microporous membrane is located on the filtrate outlet side, being provided with a space between the blood filtering material and the filtrate outlet, and being provided with a means for preventing adhesion of the blood filtering material on the filtrate outlet side.

The present invention also provides a blood filter unit as above wherein said means for preventing adhesion is a solid material arranged so as to leave liquid passages.

Figure 1:
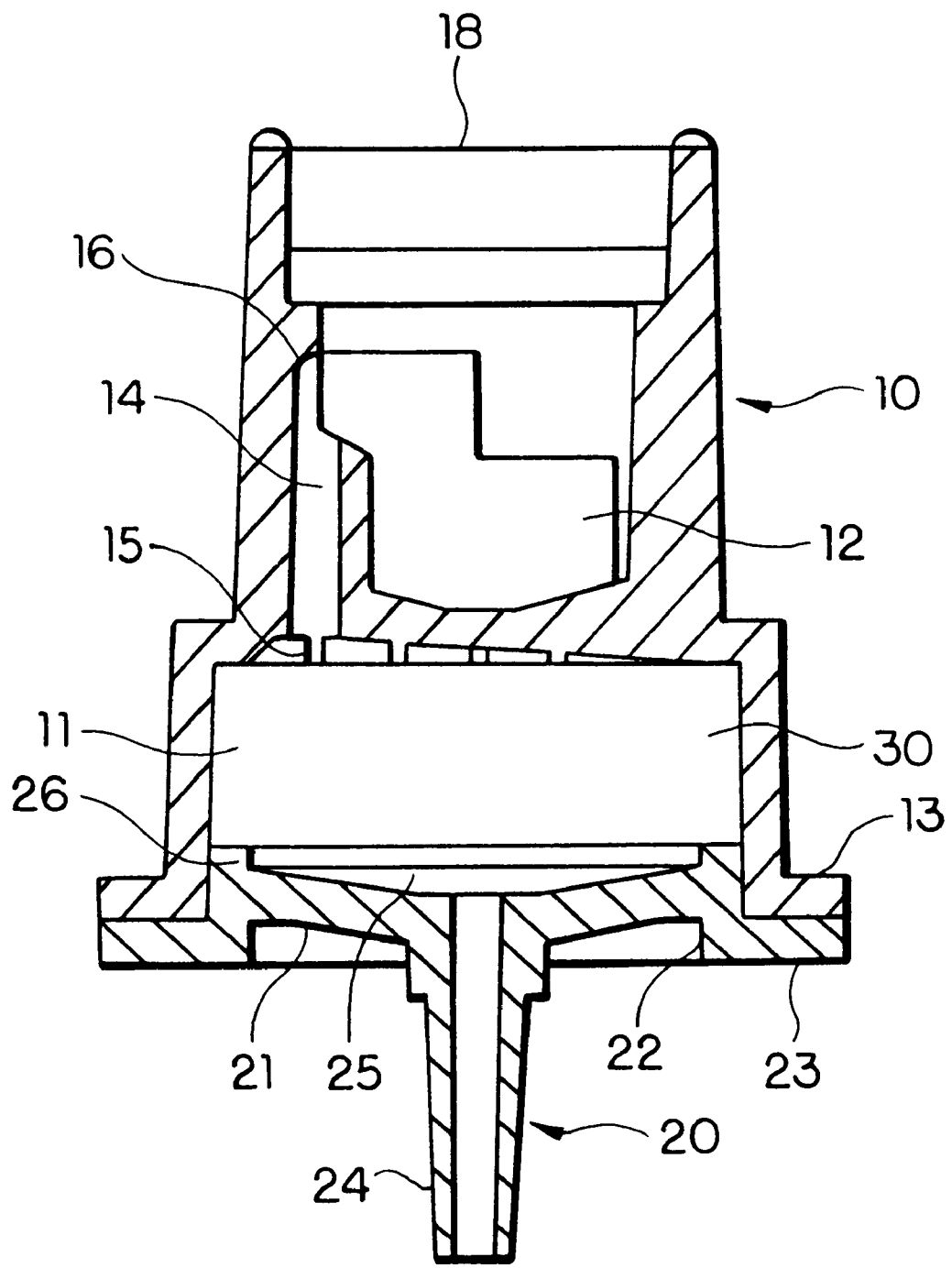
FIG. 1 is a logitudinal section of a blood filter unit embodying the invention.
Figure 2:
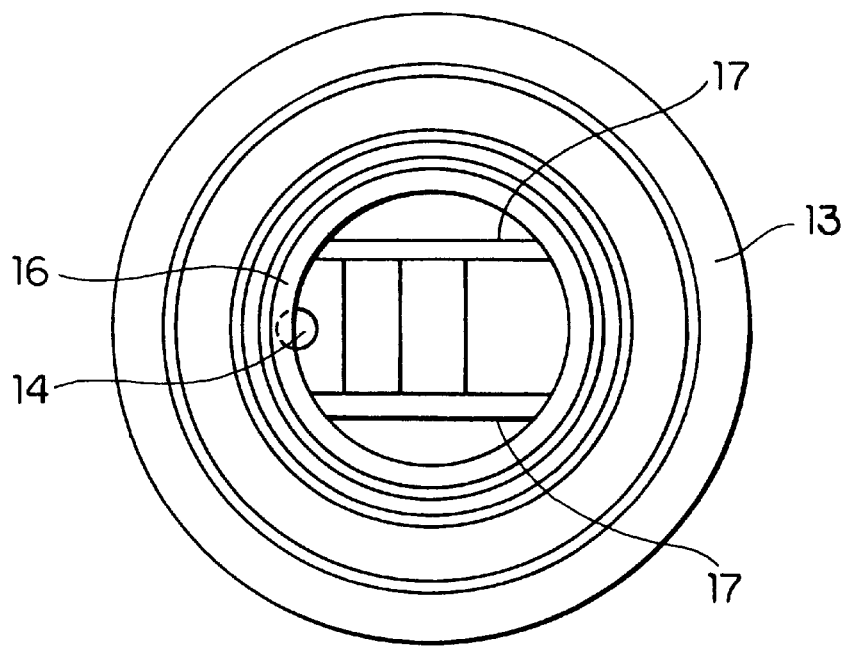
FIG. 2 is a plan view and FIG. 3 is a bottom view thereof.

10, 40, 60, 90, 120 Holder body
11, 41, 61, 91 Filter chamber
12, 52, 110, 140 Plasma receiver
13, 53, 93 Flange
14, 54, 104, 134 Plasma passage
15, 55, 105 Projection (means for preventing adhesion)
16, 56, 114 Pent-roof
17 Side wall
18, 58, 78, 116 Suction port
20, 50, 70, 100, 130 Cap
21, 42, 92 Circle plate portion
22 Short cylinder portion
23, 43, 103, 133 Flange
24, 44, 64, 94 Blood inlet
25, 45, 95 Space
26, 46, 96 Spacer
27 Rib
30 Blood filtering material
31 Glass fiber filter
32 Cellulose filter
33 Double face adhesion tape
34 Polysulfone microporous membrane
35 Flow area-regulating member
47, 97 Flap
51, 101, 131 Step
57, 115 Partition wall
80 Syringe
102 Fitting wall
111 Step portion
112 Bottom portion 123 Sheath
132 Engaging projection
135 Plasma discharge port
136 Jaw portion
141 Longitudinal channel
142 Engaging recess
150 Suction tip
151 Step portion
152 Large diameter portion
153 Rib
154 Suction port
160 Agglomerate checking member
161 Grid
162 Ring plate
163 Disc
164 Net
165 Truncated cone cylinder
166 Net

DETAILED DESCRIPTION OF THE INVENTION

Microporous membranes having blood cell-separating ability of which the surface has been made hydrophilic separate whole blood into blood cells and plasma specifically without hemolysis to the degree of substantially influencing analytical values. A suitable pore size of the microporous membrane is smaller than the retaining particle size of glass fiber filter, and is 0.2 μm or more, preferably about 0.3 to 5 μm, more preferably about 0.5 to 4.5 μm, particularly preferably about 1 to 3 μm. The void content of the microporous membrane is preferably higher, and a suitable void content is about 40 to 95%, preferably about 50 to 95%, more preferably about 70 to 95%. Illustrative of the microporous membranes are polysulfone membrane, fluorine-containing polymer membrane, cellulose acetate membranes nitrocellulose membrane, etc. The surface of the membrane may be hydrolyzed or may be rendered hydrophilic by a hydrophilic polymer or an activating agent.

The blood filtering material used in the invention comprises glass fiber filter and microporous membrane.

Preferable glass fiber filter has a density of about 0.02 to 0.3 g/cm³ preferably about 0.05 to 0.2 g/cm³ more preferably about 0.07 to 0.15 g/cm³, a retainable particle size of about 0.8 to 9 μm, preferably 1 to 5 μm. By treating the surface of glass fiber with hydrophilic polymer as disclosed in Japanese Patent KOKAI Nos. 2-208565, 4-208856, filtration proceeds more fast and smoothly. Lectin or other reactive reagent or modifier may be incorporated into glass fiber, or glass fiber may be treated therewith. Two or more glass fiber filters may be laminated.

As the fluorine-containing polymer membrane, there are the microporous matrix membrane (microporous layer) composed of polytetrafluoroethylene fibrils (fines) disclosed in WO 87/02267, Gore-Tex (W. L. Gore and Associates), Zitex (Norton), Poreflon (Sumitomo Denki), etc. Other fluorine-containing polymer sheets usable as the microporous layer include polytetrafluoroethylene microporous membranes disclosed in U.S. Pat. No. 3,368,872 (Examples 3 and 4), U.S. Pat. No. 3,260,413 (Examples 3 and 4), U.S. Pat. No. 4,201,548, etc., polyvinylidenefluoride microporous membranes disclosed in U.S. Pat. No. 3,649,505 and the like. The microporous membrane of fluorine-containing polymer may be prepared by using a single fluorine-containing polymer or blending two or more kinds of fluorine-containing polymers or further blending one or more polymers not containing fluorine or fibers therewith. As the structure, there are unstretched one, uniaxially stretched one, biaxially stretched one, nonlaminated single layer type, laminated double layer type, such as a membrane laminated to another membrane structure such as a fiber membrane. In the case of nonlaminated type microporous membrane having fibril structure or having been uniaxially or biaxially stretched, microporous membrane having a great void content and a short filtering pass can be prepared by strething. In microporous membranes having short filtering pass, clogging rarely occurs by solid components (mainly red blood cells) in blood, and the separation time of blood cells and plasma is short. As a result, accuracy in quantitative analysis is improved. The adhesive strength of adhesive used for the partial adhesion to the adjacent microporous membrane can be strengthened by providing the physical activation (preferably glow discharge or corona discharge) disclosed in U.S. Pat. No. 4,783,315 on at least one side of the microporous membrane of fluorine-containing polymer to render hydrophilic.

It is wellknown that fluorine-containing polymer microporous membranes as it is have a low surface tension. As a result, when the membrane is used as the blood cell filtering layer, aqueous liquid samples are repelled and do not diffuse nor permeate over the surface or into the inside. In the invention, the above repelling problem has been resolved by incorporating a sufficient amount of surfactant for rendering the outer surface and the inner space surface of the fluorine-containing polymer microporous membrane substantially hydrophilic thereinto. In order to impart a hydrophilic property sufficient for diffusing, permeating or moving an aqueous liquid sample over the surface or into the inside of the fluorine-containing polymer microporous membrane without repelling to the membrane, in general, it is necessary that the space surface of the membrane is coated with a surfactant in an amount of about 0.01 to 10%, preferably about 0.1 to 5%, more preferably about 0.1 to 1% of the void volume of the membrane. For example, in the case of a fluorine-containing polymer microporous membrane 50 μm in thickness, a preferred amount of surfactant to be impregnated is usually in the range of 0.05 to 2.5 g/m². As the method of impregnating surfactant into a fluorine-containing microporous membrane, a common method comprises immersing the fluorine-containinng microporous membrane in the surfactant solution dissolved in a low boiling point (a preferable boiling point is in the range of about 50° C. to about 120° C. ) organic solvent (e.g. alcohols, esters, ketones) to permeate into the inner spaces of the membrane substantially sufficiently, taking the membrane out of the solution slowly, and then drying by blowing air (preferably warm air).

As the surfactant for rendering the fluorine-containing polymer microporous membrane hydrophilic, the surfactant may be nonionic, anionic, cationic or ampholytic. However, nonionic surfactants are advantageous for the multilayer analytical elements for analyzing whole blood samples, because nonionic surfactants have a relatively low hemolytic activity among the above surfactants. Suitable nonionic surfactants include alkylphenoxypolyethoxyethanol, alkylpolyether alcohol, polyethyleneglycol monoester, polyethyleneglycol diester, higher alcohol-ethylene oxide adduct (condensate), polyol ester-ethylene oxide adduct (condensate), higher fatty acid alkanol amide, etc. Examples of the nonionic surfactant are as follows: As the alkylphenoxypolyethoxyethanol, there are isooctylphenoxypoly-ethoxyethanols (Triton X-100; containing 9–10 hydroxyethylene units on average, Triton X-45; containing 5 hydroxyethylene units on average) and nonylphenoxypolyethoxy ethanols (IGEPAL CO-630; containing 9 hydroxyethylene units on average, IGEPAL CO-710; containing 10–11 hydroxyethylene units on average, LENEX 698; containing 9 hydroxyethylene units on average). As the alkylpolyether alcohol, there are higher alcohol polyoxyethylene ethers (Triton X-67; CA Registry No. 59030-15-8), etc.

The fluorine-containing polymer microporous membrane may be rendered hydrophilic by providing one or more water-insolubilized water-soluble polymers in its porous spaces. The water-soluble polymers include oxygen-containing hydro carbons, such as polyacrylamide, polyvinylpyrrolidone, polyvlnylamine and polyethylenamine, negative charge-containing ones such as polyvinyl alcohol, polyethylene oxide, polyethylene glycol, methyl cellulose, ethyl cellulose, hydroxyethyl cellulose and hydroxypropyl cellulose, nitrogen-containing ones, such as polyacrylic acid, polymetacrylic acid and polystyrene sulfonic acid, and the like. The water-insolubilization may be conducted by heat treatment, acetal-inducing treatment, esterification, chemical reaction by potassium dichromate, crosslinking by ionizable radiation, or the like. Details are disclosed in Japanese Patent KOKOKU Nos. 56-2094 and 56-16187.

The polysulfone microporous membrane can be prepared by dissolving polysulfone into dioxane, tetrahydrofuran, dimethylformamide, dimethylacetamide, N-methyl-2-pyrolidone or a mixed solvent thereof to obtaine a raw liquid for forming film, casting into film by flowing directly into a coagulating solution, washing, and then drying. Details are disclosed in Japanese Patent KOKAI No. 62-27006. In addition, polysulfone microporous membranes are also disclosed in Japanese Patent KOKAI Nos. 56-12640, 56-86941, 56-154051, etc., and they are applicable to the invention. The polysulfone microporous membrane can be rendered hydrophilic, similar to the fluorine-containing polymer, by incorporating surfactant or providing water-insolubilized water-soluble polymer.

As the other nonfibrous microporous membranes, blushed polymer membranes composed of a cellulose ester, such as cellulose acetate, cellulose acetate/butyrate or cellulose nitrate, disclosed in U.S. Pat. No. 3,992,158 or U.S. Pat. No. 1,421,341 are preferable. Microporous membranes of polyamide, such as 6-nylon or 6,6-nylon, or polyethylene, polypropylene, or the like are also usable. Other nonfibrous microporous membranes usable include continuous microspace-containing porous membranes where polymer particulates, glass particulates, diatomaceous earth or the like are joined by a hydrophilic or non-water-adsorptive polymer, such as disclosed in U.S. Pat. No. 3,992,158, and U.S. Pat. No. 4,258,001.

Suitable effective pore size of the nonfibrous microporous membrane is 0.2 to 10 μm, preferably 0.3 to 5 μm, particularly preferably 0.5 to 5 μm. The effective pore size of the nonfibrous porous membrane in the invention is the pore size measured by the bubble point method according to ASTM F316-70. In the case that the nonfibrous porous membrane in a membrane filter composed of blushed polymer prepared by the phase separation method, the liquid passages in the thickness direction are, in general, the narrowest at the free surface (glossy face) in the manufacturing process of the membrane, and the pore size in section of each liquid passage stipulated a circle is the smallest near the free surface. The minimum pore size of passages in the thickness direction per unit area has a distribution in facial direction of the membrane filter, and the maximum value determines filtration performance. In general, it is determined by the limit bubble point method.

As mentioned above, in the membrane filter composed of blushed polymer prepared by the phase separation method, liquid passages in the thickness direction become the narrowest at the free surface (glossy face) in the manufacturing process of the membrane. In the case of using the membrane as the nonfibrous porous membrane of the filtering material of the invention, it is preferable to face the glossy face of the membrane filter toward the side to discharge the plasma portion.

A third filtering material may be incorporated into the blood filtering material. The third filtering material may be filter paper, nonwoven fabric, woven fabric such as plain weave fabric, knitted fabric such as tricot fabric, etc. Among them, woven fabric and knitted fabric are preferred. The woven fabric or the like may be treated by glow discharge as disclosed in Japanese Patent KOKAI No. 57-66359, The third filtering material is preferably interposed between the glass fiber filter and the microporous membrane.

Preferable microporous membranes are polysulfone membrane, cellulose acetate membrane and the like, and particularly preferred one is polysulfone membrane. In the blood filtering material of the invention, the glass fiber filter is located on the blood inlet side and the microporous membrane in located on the filtrate outlet side. The most preferable blood filtering material is a laminate of the glass fiber filter, cellulose filter and polysulfone membrane laminated in this order from the blood inlet side.

In the case that the filtering material used in the invention is a laminate, respective layers may be integrated by joining each other using partially disposed (e.g. spots) adhesive, according to disclosures in Japanese Patent KOKAI Nos. 62-138756-8, 2-105043, 3-16651, etc.

In the filtering material of the invention, it is thought that the filter material does not trap blood cells only by the surface, but catches to remove blood cells gradually by entangling at first large blood cell components and then smaller blood cell components in the space structure with permeating in the thickness direction in total of the filtering material, called the volumetric filtration.

The quantity of whole blood filterable by this system is greatly influenced by the void volume existing in glass fiber filter and the volume of blood cells in the whole blood. When the density of the glass fiber filter is high (pore size to retain particles is small), erythrocytes are trapped in the vicinity of glass fiber filter surface, voids in the glass fiber filter are clogged in a very thin region from the surface, and accordingly, filtration does not proceed thereafter. As a result, recovered plasma volume by filtration is small. On that occasion, when the filter material is sucked by stronger suction in order to increase recovered plasma volume, blood cells are destroyed, i.e. hemolyzed. That is, the filtration becomes similar to surface filtration, and utilization rate of void volume of the filter is low.

As an indicator corresponding to void volume or filtrate volume of plasma, water permeation speed is suitable. The water permeation speed is determined by putting a glass fiber filter with a definite area in a closed filter unit of which the inlet and outlet can be connected by a tube, adding a definite volume of water, and pressurizing or sucking at a constant pressure. The water permeation speed is filtrate volume per unite area and time, and expressed by ml/sec.

For example, glass fiber filter 20 mm ø in diameter is put in a filter unit, and a 100 ml syringe containing 60 ml water is connected to the top of the filter unit. Water flows down naturally, and volume of water passing through the glass filter from 10 sec to 40 sec after starting is measured as the water peameation volume, and the water permeation speed per unit area is calculated from it.

Glass fiber filters particularly suitable for plasma separation are having a water permeation speed of about 1.0 to 1.3 ml/sec, and illustrative of the glass fiber filters are Whatman GF/D, Toyo Roshi GA-100, GA-200 and the like. Furthermore, the glass fiber filter can be prepared by suspending glass fibers of a commercial glass fiber filter in hot water, and then making the glass fibers into a low density sheet (density: about 0.03 g/cm$^3$) on a nylon net. The glass fiber filter thus prepared shows good plasma separating ability.

A suitable thickness of the glass fiber filter varies according to the plasma volume to be recovered and density (void content) and area of the glass fiber filter. A necessary amount of plasma for analyzing plural items using dry analytical elements is 100 to 500 $\mu$l. In practical viewpoint, a glass fiber filter having a density of about 0.05 to 0.2 g/cm$^3$ and an area of 1 to 5 cm$^3$ is suitable. In this case, a suitable thickness of the glass fiber filter is about 1 to 10 mm, preferably about 2 to 8 mm, more preferably about 2 to 6 mm. The above thickness can be made by superposing 1 to 10 sheets, preferably 2 to 6 sheets of glass fiber filter.

A suitable thickness of the microporous membrane is about 0.05 to 0.3 mm, preferably about 0.1 to 0.2 mm, and the number of the microporous membrane is usually one. However, two or more sheets of microporous membrane may be used, if necessary.

The holder accommodates the blood filtering material, and is provided with a blood inlet and a filtrate outlet. The holder is, in general, formed of a body accommodating the blood filtering material and a cap, and every one is provided with at least one aperture. One is used as the blood inlet, optionally further as a pressuring port, and the other is used as the filtrate outlet, optionally further as a suction port. A suction port or a pressurizing port may be provided separately. In the case that the holder is rectangular and is provided with the cap on a side of the holder, both of the blood inlet and the filtrate outlet may be provided on the holder body.

The volume of the filter chamber which accommodates the blood filtering material is necessary to be greater than the total volume of the blood filtering material both in a dry state and in a swelled state upon absorbing a sample (whole blood). When the volume of the filter chamber is smaller than the total volume of the blood filtering material, filtration does not proceed efficiently and hemolysis occurs. A suitable ratio of the volume of the filter chamber to the total volume of the blood filtering material in a dry state is, in general, 101 to 300%, preferably 110 to 200%, more preferably 120 to 150%, although the ratio varies according to the swelling degree of the filtering material.

Besides, it is necessary that the periphery of the blood filtering material is closely fitted to the wall of the filter chamber so as not to form a bypass of whole blood without passing the filtering material.

In an aspect of the blood filter unit of the invention, a means for preventing adhesion of the blood filtering material on the filtrate outlet side is provided. The means is to separate the blood filtering material from the filtrate outlet side of the holder so as to proceed filtration in broader area, preferably over all face of the blood filtering material. Such a means includes to render the filtrate outlet side of the holder concave, such as in cone or partial sphere, to provide a solid material arranged so as to leave liquid passages, such as plural projections, about 1 to 20 projections, preferably 3 to 10 projections, per 1 cm$^2$ on the filtrate outlet side of the holder, a spacer, such as net, grains or ring(s), and the like. In the case of forming concave, the filtrate outlet is preferably provided on the deepest position.

Figure 7:
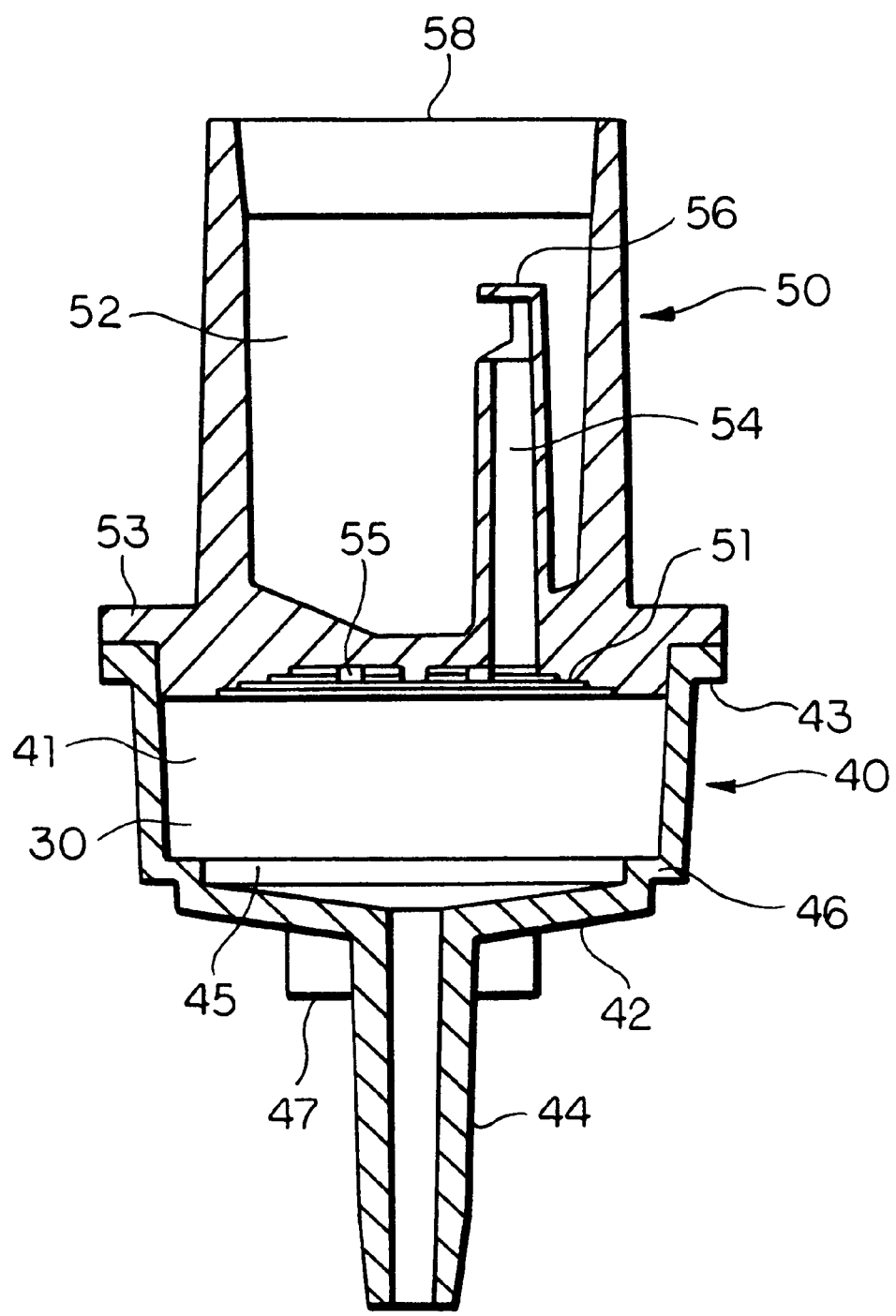
FIG. 7 is a longitudinal section of another blood filter unit also embodying the invention.

The following 4 holders were prepared. ① The blood filtering material was in contact with the filtrate outlet side, and the filtrate outlet was provided at the center of the filtrate outlet side, or ② the filtrate outlet was provided in the vicinity of the periphery of the filtrate outlet side. ③ A step-formed concave (1 mm in depth) was formed as shown in FIG. 7, and the filtrate outlet was provided at the center, or ④ the filtrate outlet was provided in the vicinity of the periphery. Using the above holders, recovered volume of plasma was measured and found to be ① 50 $\mu$l, ② 40 $\mu$l, ③ 243 $\mu$l and ④ 330 $\mu$l The shape of the projections may be column, square column, cone and truncated thereof, pyramid and truncated thereof, mushroom, irregular form, or any other form, but the top of the projections is preferably flattened or rounded.

A suitable total contact area of the solid material arranged so as to leave liquid passages, such as the top of the projections with the blood filtering material upon filtering is about 1 to 50%, preferably about 1 to 10% of the surface area of the blood filtering material of effective filtering area, i.e. except periphery for holding the blood filtering material. Since the amount of the blood filtered by the blood filter unit of the invention is small, a suitable space left by the means for preventing adhesion upon filtering blood is about 1 to 500 $\mu$l, preferably about 1 to 100 $\mu$l. The filtrate outlet side of the holder is preferably formed in a funnel shape so as to facilitate discharge of plasma which is filtrate.

A plasma receiver which receives the plasma may be provided on the filtrate outlet side of the holder. In the viewpoint of designing an analyzer which analyzes the plasma obtained by the blood filter unit of the invention, it is preferable to suck the plasma by the analyzer at the center of the holder, and as a result, a passage of plasma to the plasma receiver is formed excepting the center. When the passage is formed in the vicinity of the periphery of the plasma reciever, molding is facilitated. Moreover, troubles of entering plasma into a suction duct can be prevented which tends to occur in the case of low viscosity plasma. Since it is possible to spout plasma from the plasma passage by suction in the case of a small hematocrit value blood, a baffle, such as a pent-roof, is preferably provided at the exit of the passage. The bottom of the plasma receiver is preferably inclined, such as in a form of reversed cone so as to facilitate the suction by a suction nozzle of an analyzer. Moreover, since recovered volume of plasma considerably varies according to hematocrit value, it is preferable to provide an over flow structure.

The capacity of the plasma receiver may be about 10 $\mu$m to 1 ml.

In order to examine effects of the space formed on the blood inlet side of the holder, the following experiments were carried out.

Shape of Inlet Side of Holder and Recovery of Plasma (1) The following three structures wherein blood was supplied from the underside were examined.

① The bottom is flat, and sucked blood immediately contacts glass fiber filter.

② The bottom is in a funnel shape, and sucked blood is spread to an area in a certain degree and then contacts glass fiber filter.

③ A spacer (1 mm in thickness) is interposed between the bottom and glass fiber filter, and sucked blood is once accumulated under the bottom. By further sucking, the level of blood elevates, and blood contacts over all area of glass fiber filter almost simultaneously.

(2) Blood-Drawing

Vein blood was drawn from a healthy woman using a 10 ml vacuum blood-drawing tube containng heparin (Terumo), and 2 ml was pipetted into each sample tube made of plastic. Hct value was 41%.

(3) Assembling of Filter Unit

Six sheets of glass fiber filter (GF/D, Whatman) punched into disc 19.7 mm ø in diameter were put in a filter holder as shown in FIG. 1 (except the upper structure of the body), and a polysulfone membrane (Fuji Photo Film Co., Ltd.) was superposed thereon. A joint for sucking air was attached further thereon, and connected to a small size peristaltic pump.

(4) Filtration of Blood

A silicone tube 4 cm in length was connected to the blood inlet of the filter unit assembled in the above (3), and the end of the tube was inserted into the sample tube containing a blood sample prepared in the above (2), and fixed in almost vertical direction.

The suction speed of the peristaltic pump was set at 2.8 ml/sec, and suction was conducted twice each for 10 seconds. The interval between the first suction and the second suction was 1 second. Plasma was separated and accumulated in the plasma receiver.

(5) Results

As a result, in ①, obtained plasma volume was very small, and the degree of hemolysis was great, and on the other hand, in ③, a great volume of plasma with good quality was recovered. In ②, plasma obtained was intermediate betweeen ① and ③, and recovered volume of the plasma was insufficient.

As mentioned above, it is preferable to provide a space also on the blood inlet side so that filtration proceeds over all face of the blood filtering material. Thereby, first, air is sucked over all face of the blood filtering material, and as a result, blood is sucked and filtered with spreading over the entire face. Since the blood filtering member on the blood inlet side acts in the direction to move apart from the blood inlet face of the holder upon filtering, the space can be formed by a spacer, such as a ring rib or several projections, for holding the blood filtering material at the periphery on the inner wall of the holder. It is also possible to project the periphery of the cap toward the blood filtering material side, and the projection is functioned as the spacer. A suitable volume of the space between the blood filtering material and the blood inlet face of the holder is about 100 to 500 µl, preferably about 100 to 200 µl upon filtering.

The filter unit of the invention is made into a closed structure except the blood inlet and the filtrate outlet by attaching a cap to the holder body.

As the material of the holder, thermoplastic or thermosetting plastics are preferable. Illustrative of the plastics are high impact polystyrene, methacrylate resin, polyethylene, polypropylene, polyester, nylon, polycarbonate, various copolymers, etc. The material may be transparent or opaque.

Fitting of the cap to the holder body may be any means, such as adhesion using adhesive or fusion welding. On that occasion, either periphery of the holder body or of the cap is located on the inside, or both peripheries are butted. The fitting may be in a state of detachable utilizing screws or the like.

The shape of the blood filtering material is not restricted, but disc and polygon is preferable in view of production. By rendering the size of the blood filtering material slightly greater than the inside section of the holder body (i.e. filter chamber), breakthrough of blood at the periphery of the filtering material can be prevented. To render the shape square is preferable because of no generation of cutting loss.

In another aspect of the blood filter unit of the invention, a flow area-regulating member is provided on the blood filtering material on the filtrate outlet side which is, in general, the microporous membrane. The flow area-regulating member is made of liquid-impermeable material, and has an opening having an area smaller than the blood filtering material thereby regulates so that filtrate flows out through the opening. A suitable area of the opening is about 20 to 90%, preferably about 50 to 90% of the blood filtering material area on the filtrate outlet side.

The flow area-regulating member can be made by various commercial adhesive tape, plastic film, thin plastic sheet or the like, and adhesive may be applied to the adhering face of the blood filtering material.

In still another aspect of the blood filter unit of the invention, anticoagulant is provided in the passage of blood.

The anticoagulant inhibits blood coagulation caused by deposition of fiblin from blood, and exemplary anticoagulants are heparin, ammonium, sodium, lithium, potassium, plasmin, EDTA, sodium oxalate, etc. Heparin is particularly preferable because of having a high ability to inhibit deposition of fiblin. The amount to be used of the anticoagulant is necessary for inhibiting coagulation of recovered plasma, and accordingly, depends on the volume of recovering plasma. In general, a suitable amount of the anticoagulant is about 0.01 to 1 unit, preferably 0.05 to 0.5 unit.

The passage of blood is from the blood entrance to the filtrate exit of the blood filter unit, and when a plasma receiver is provided, the plasma receiver is also included. The antioagulant may be located at any part of the blood passage. However, in order to decrease the influence on liquid flow, it is preferable to incorporate the anticoagulant into the blood filtering material or plasma receiver. The anticoagulant is preferably in a dry state so as not to deteriorate during storage. The anticoagulant is in a state capable of contacting blood or plasma upon filtering and dissolving thereinto. For example, in the case of the blood filtering material, the anticoagulant is impregnated in one or more layers followed by drying. In the case of putting in a plasma receiver, one drop of an aqueous solution of anticoagulant, such as heparin, is dropped in the plasma receiver and then dried. In order to prevent flying away of the dried matter of the anticoagulant, the antiocoagulant may be wrapped by a film of water-soluble polymer, such as PVA or PVP, or impregnated into fibers or the like and then dried. The wrapped matter or impregnated matter is put in or fixed to the plasma receiver.

An agglomerate checking member may be attached to the blood inlet of the blood filter unit. The agglomerate checking member has a sampling port formed of a member having a plurality of holes for passing liquid, such as net or grid. A suitable diameter of the hole is about 100 µm to 5 mm. It is effective to provide the sampling port extended over the lower side portion in addition to the bottom of the agglomerate checking member. Examples of the agglomerate checking member are illastrated in FIGS. 20–23.

Figure 20:
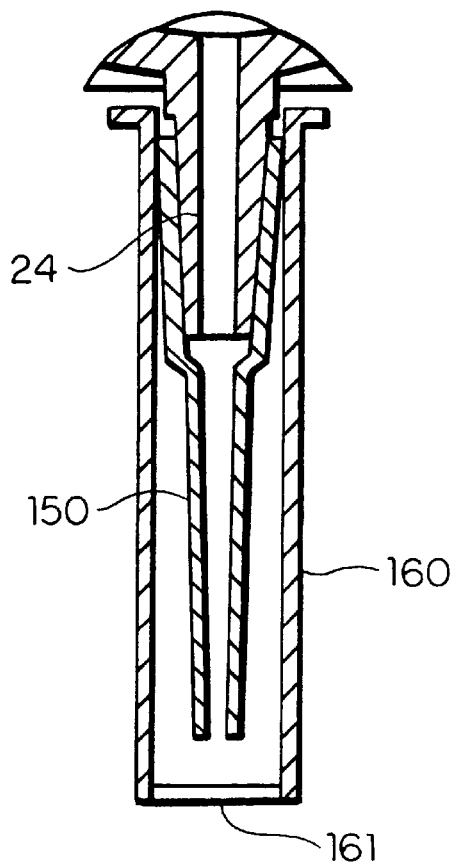
FIG. 20 is a longitudinal partial section around the suction tip to which an agglomerate checking member is attached.
Figure 21:
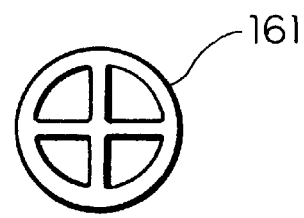
FIG. 21 is a bottom view of the agglomerate checking member.

The agglomerate checking member 160 of FIG. 20 is cylindrical, and as shown in FIG. 21, a cross-shaped grid 161 is provided on the end opening which is the suction part.

Figure 22:
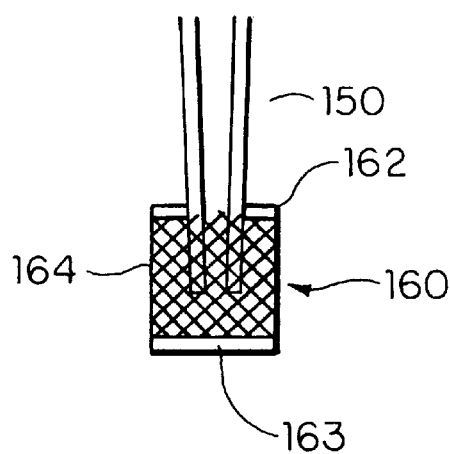
FIG. 22 is a side view of another agglomerate checking member.

The agglomerate checking member 160 of FIG. 22 is composed of an upper ring plate 162, a bottom disc 163, and a circunferential net 164. A suction tip 150 is inserted into the opening of the ring plate 162, and bonded by fusion.

Figure 23:
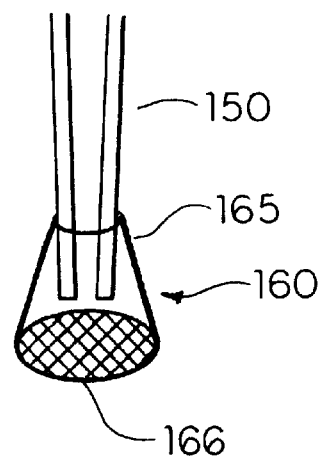
FIG. 23 is a side view of still another one.

The agglomerate checking member 160 of FIG. 23 is composed of a truncated cone cylinder 165 and a net 166 attached to the bottom. A suction tip 150 is inserted into the upper opening of the truncated cone cylinder 165, and bonded by fusion.

The material of the agglomerate checking member can be selected from those listed as the holder material.

In a further aspect of the blood filter unit of the invention, the plasma receiver is separated from the holder body and cap, and arranged detachable therefrom. The connecting structure between the plasma receiver and the holder is preferably detachable by one action, and accordingly, to connect by utilizing engaging or fitting is preferable. The detaching direction may be vertical, horizontal or slightly rotating upward. The plasma receiver can be used as a sample vessel for analyzer. A cover may be attached to the receiver in order to prevent evaporation of moisture.

Upon using the blood filter unit of the invention, blood is supplied to the blood inlet, and filtrate which is plasma or serum discharged from the filtrate outlet is recovered. A suitable supply volume of blood is about 1.2 to 5 times, preferably about 2 to 4 times, as much as the volume of the blood filtering material. It is preferable to accelerate filtration by pressurizing from the blood inlet side or sucking from the filtrate outlet side. As the sucking means, to use a peristaltic pump or a syringe. A suitable moving distance of the piston of a syringe is so that the moving volume of the piston becomes about 2 to 5 times that of the filtering material. A suitable moving speed is about 1 to 500 ml/min, preferably 20 to 100 ml/min, per 1 $cm^2$. The blood filter unit after use is usually throwaway.

Plasma or serum obtained by the blood filter unit is subjected to conventional analysis.

By using the blood filter unit of the invention, a volume of plasma or serum necessary for analysis can be obtained, irrespective of hematocrit value. The blood filter unit is particularly effective for separating plasma or serum from a high hematocrit blood such as a hematocrit value of 50 or more, and is effective for the analysis of plural items using dry analytical elements.

EXAMPLES

Example 1

A blood filter unit illustrated in FIGS. 1–6 was prepared. The filter unit was composed of a holder body 10 and a cap 20, as shown in FIG. 1 which illustrates an assembled state of the filter unit.

Figure 3:
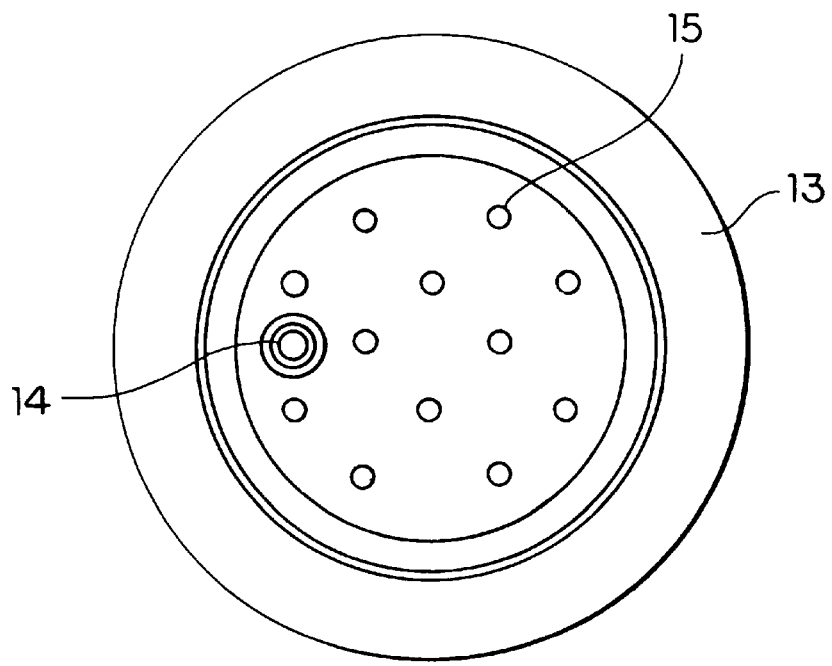

The holder body 10 is cylindrical consisting of a small diameter portion and a large diameter portion connected thereto. The upper portion is composed of a plasma receiver 12 and a connecting portion to suction side, and the lower portion becoms a filter chamber 11 for accommodating blood filtering material(s) 30. The size of the filter chamber 11 is 19.5 mm in inside diameter and 10 mm in depth. Since the upper part of the cap 20 enters there up to 3 mm in height, the height of the filter chamber becomes 7 mm. A flange 13 for connecting the cap 20 is formed outward on the outside of the lower end of the holder body 10. The entrance of plasma passage 14 is provided at the ceiling of the filter chamber 11 near the left end in FIG. 1, and the ceiling is formed into a thin funnel shape wherein the entrance is provided on the top position. The height between the periphery and the entrance is 1 mm. As shown in FIG. 3, 12 protections 15 are formed on the ceiling at almost the same interval. Each projection 15 is short rod, and the lower end is cut so as to position at the same plane. Periphery of the end of each projection 15 is cut off.

A pent-roof 16 is provided at the exit of plasma passage 14, and the underside of the pent-roof 16 is formed in an arc-shaped to prevent spouting upward of discharged plasma. A plasma receiver 12 is formed by partitioning the cylindrical holder body 1 by two side walls 17 in parallel interposing the exit of the plasma passage so as to obtain a sufficient depth even in a small plasma volume. The upper end of the holder body is opened, and it becomes a suction port 18 when connected to an analyzer (not illustrate). The upper end (suction port 18) of the holder body is rounded in order to ensure liquid-tight ability after connecting.

A cap 20 is composed of circle plate portion 21 in a thin funnel shape located at center, short cylinder portion 22 formed surrounding the periphery of the circle plate portion 21, a flange 23 formed outward on the outside of the lower end of the short cylinder portion 22, and a nozzle-shaped blood inlet 24 extended downward from the center of the circle plate portion 21. The diameter of the circle plate portion is 17 mm, the depth in the funnel portion is 1 mm, the height of the short cylinder portion 22 is 4.5 mm, and the outer diameter of the flange 23 is 28 mm. The connecting position of the circle plate portion 21 to the short cylinder portion 22 is made lower than the upper edge of the short cylinder portion 22 by 1 mm, and thereby, the upper end functions as a spacer 26 for separating the underside of the blood filtering material 30 from the top face of the funnel-shaped circle plate portion 21 to form a space 25. On the top face of flange 23 facing the flange 13 of the holder body 10, a rib 27 is formed in ring shape.

The rib 27 collects ultrasonic energy upon fusion bonding the flanges 13, 23 by ultrasonic wave to ensure liquid-tight ability at the joined portion.

Six sheets of glass fiber filter (Whatman GF/D) punched into disc 19.7 mm in diameter were put in the filter chamber 11 with pressing by a force of about 80 g, and a polysulfone microporous membrane (Fuji Photo Film Co., Ltd.) was superposed thereon. Respective filter layers were contact with each other lightly. Then, the cap 20 was fitted, and joined by ultrasonic welding.

Thus, a blood filter unit was completed.

Example 2

Figure 8:
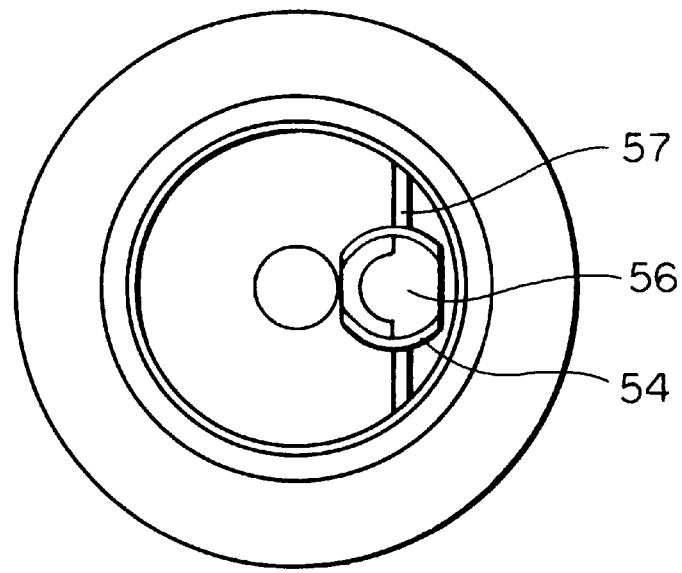
FIG. 8 is a plan view and FIG. 9 is a bottom view thereof.
Figure 9:
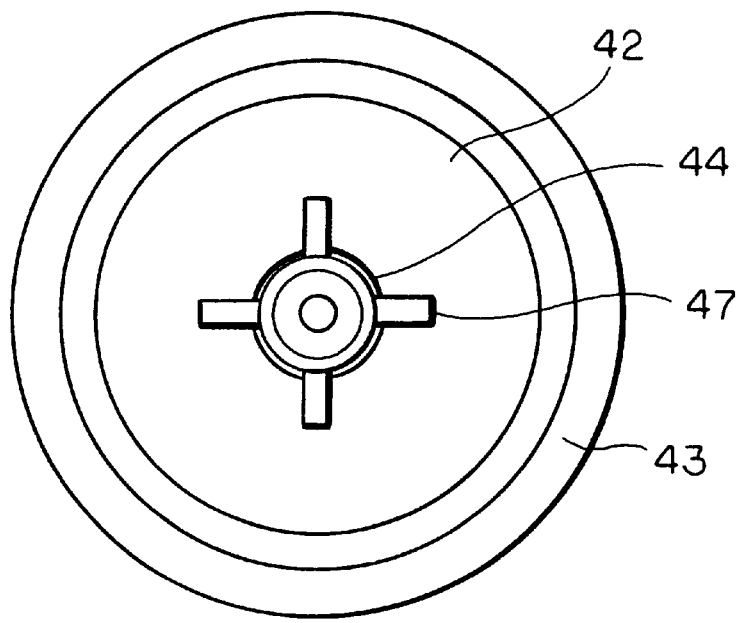

A blood filter unit illustrated in FIGS. 7–9 was prepared. The filter unit was composed of a holder body 40 and a cap 20, as shown in FIG. 7 which illustrates an assermbled state of the filter unit.

Figure 4:
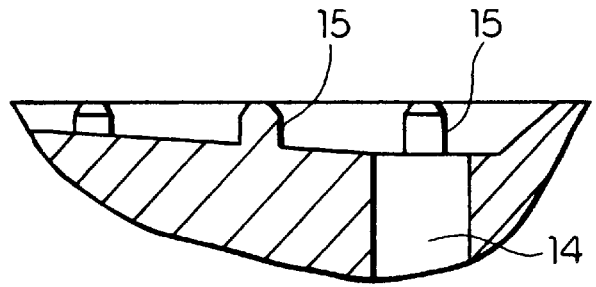
FIG. 4 is an enlarged partial section indicating the shape of projections.
Figure 5:
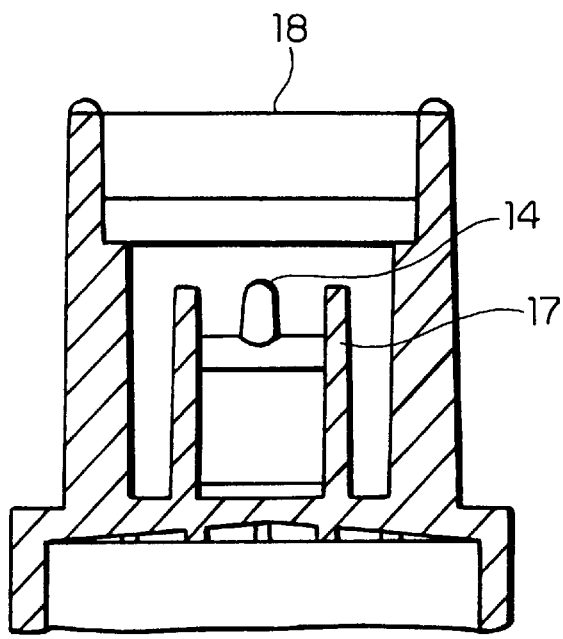
FIG. 5 is a longitudinal section of an upper part of the holder body cut in the direction rectangular to FIG. 1 seen toward a plasma passage.
Figure 6:
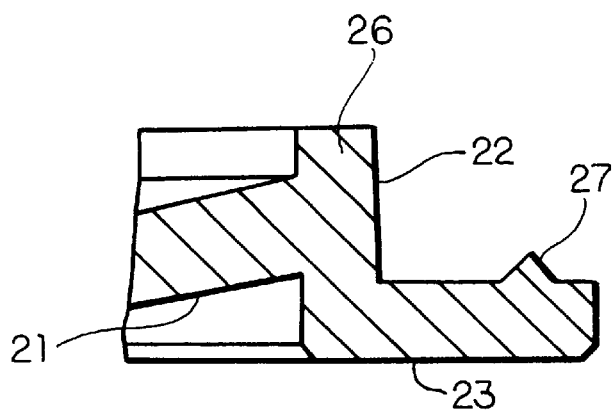
FIG. 6 is an enlarged partial section indicating a flange portion of a cap.

The holder body 40 is formed of a filter chamber 41 for accommodating blood filtering material(s) 30 and a flange 43 formed outward at the upper end of the filter chamber 41. The bottom of the filter chamber 41 is made by a thin funnel-shaped circle plate portion 42 with a step portion near the periphery, and a nozzle-shaped blood inlet 44 is extended downward from the center of the circle plate portion 42. The above step portion functions as a spacer 46 for separating the underside of the blood filtering material 30 from the funnel-shaped circle plate portion 42 to form a space 45. As shown in FIGS. 7 and 9, 4 flaps 47 are formed at the base portion of the blood inlet 44 at almost the same intervals. The flaps 47 are for holding a sample tube (not illustrated) by fitting thereto.

The underside of the bottom of the cap 50 is recessed to form an upper space wherein 4 steps 51 are formed in concentric circle shape. Five projection 55 are projected downward as the means for preventing adhesion in the central portion in the shape of 5 spots in a die. A plasma passage 54 in a smokestack-shaped with shaving in parallel stands upward from near the middle point between the center and periphery, and a pent-roof 56 which prevent spouting upward of discharged plasma is provided at the top of the plasma passage 54 in the horizontal direction. As shown FIG. 8, the pent-roof 56 has a shape of a combination of two half circles. The half circle on the periphery side is in consistent with the outer wall of the plasma passage 54, and the half circle on the center side is in consistent with extension of the inner wall of the plasma passage 54.

A partition wall 57 is formed in straight interposing the plasma passage in order to ensure a sufficient depth even in a small plasma volume. The upper end of the plasma receiver 52 is opened, and it becomes a suction port 58. A flange 53 is formed outward near the lower end of the cap 50, and the flange 53 is joined to the flange 43 of the holder body by ultrasonic welding. A rib (not illustrated) is formed on the face of the flange 53 facing the flange 43 of the holder body so as to ensure liquid-tight ability at the joined portion.

Example 3

Figure 10:
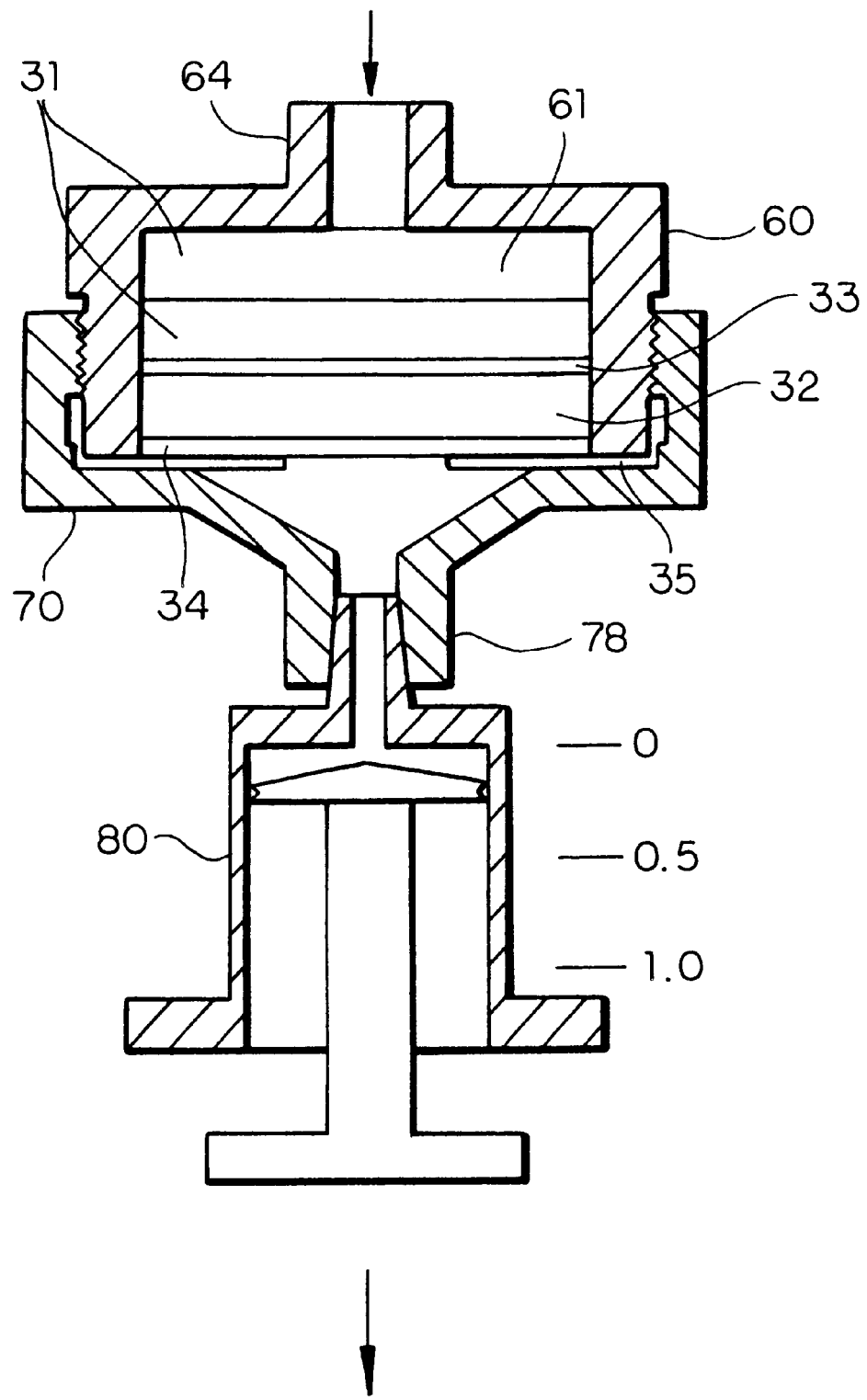
FIG. 10 is a longitudinal section of another blood filter unit embodying the invention.

A blood filter unit illustrated in FIG. 10 was prepared. The filter unit was in short cylinder form 25 mm ø in outer diameter and 20 mm ø in inner diameter, and was composed of a holder body 60 and a cap 70.

The underside of the holder body 60 is opened, and a filter chamber 61 is formed therein. A screw groove for screwing the cap 70 thereon is cut at the lower part of the outer peripheral wall. The top face is closed, and a blood inlet 64 is prejected from the center. A screw groove is cut also at the upper part of the inner wall of the cap 70.

The central part of the cap 70 is inflated in funnel shape and a suction port 78 is projected downward from the center of the cap 70. A syringe 80 for the suction of blood is fitted into the suction port 78.

The above filter holder 60 was turned, and superposed 2 sheets of glass fiber filter (Whatman GF/D) 31 punched into disc having a diameter of 20.1 mm ø ware put in the filter chamber 61. The glass fiber filter 10 had an areal weight of 122.4 g/m$^2$, a thickness of 1.3 mm and a density of 0.094 g/cm$^3$. A cellulose filter ("Cytosep", made by Cytosep) 32 having a thickness of 1 mm and a diameter of 20.1 mm ø was fixed thereon by using a double face adhesive tape 33 having a diameter of 20.1 mm provided with an opening 13 mm ø in diameter. A polysulfone microporoces membrane ("PS", Fuji Photo Film Co, Ltd.) 34 having a pore size of 2 μm, a thickness of 0.15 mm and a diameter of 20.1 mm ø was superposed thereon, and an adhesive vinyl tape 35 having a diameter of 20.1 mm ø provided with an opening 8 mm ø in diameter at the center was superposed further thereon and pressed to join it.

② Blood-Drawing 5 ml of whole blood was drawn from a healthy man with heparin. Hematocrit value of the blood was measured and found to be 44%.

③ Preparation of HL Agent

Lithium sulfate monohydrate ($Li_2SO_4 \cdot H_2O$) was weighed, and dissolved in distilled water to obtain a 2 mol/l aqueous lithium sulfate solution.

④ Preparation of HL Agent-Added Whole Blood

30 μl of the HL agent solution prepared in ③ was pipetted into a 2 ml sample tube, and 1.5 ml of the whole blood with heparin was added thereto. Hematocrit value was measured and found to be 30%.

⑤ Filtration of Blood

The whole blood prepared in ④ was introduced into the filter unit assembled in ①, and sucked at a suction speed of 600 μl/min for 20 seconds. As a result, plasma was separated and accumulated on the polysulfone membrane in the inflated portion of the cap.

⑥ Recovery of Separated Plasma

Using a micropipette, separated plasma was taken out, and the volume of the plasma was measured. The volume was about 395 μl. Hemolysis did not occur.

Since the volume of the glass fiber filters was 628 mm$^3$, the half was 314 mm$^3$ (i.e. 314 μl). By this example, it was confirmed that plasma in an amount of ½ or more of the volume of glass fiber filter(s) can be recovered easity and surely.

Example 4

Blood was drawn from healthy women to obtain 20 ml whole blood with heparin. Hematocrit value of the blood was measured and found to be 41%. A part of the blood was centrifuged to obtain high hematocrit whole blood samples by separating plasma. The plasma was added to the original whole blood, and a low hematocrit whole blood was prepared. Thus, 5 types (No.1–No.5) of whole blood samples different in hematocrit value were prepared.

To each No.1–No.5 samples, 2 mol/l $Li_2SO_4$ was added in an amount of 50 μl per 1 ml whole blood. The sample was filtered with suction using the same filter unit as Example 3, provided that the whole blood sample was introduced from the upside, and a 5 ml syringe was fitted into the suction port located on the underside. Suction was carried out in a displacement of 800 μl for 30 seconds. The volume of the glass fiber filter was 185 mm$^2$ (i.e. 185 μl). Recovered volumes of each sample are summarized in Table 2.

TABLE 2

| Hct (%) | | 20 | 41 | 48 | 59 | 68 |
|---|---|---|---|---|---|---|
| Recovered Plasma Volume (μl) | Inventive Example 2 | 540 | 410 | 325 | 215 | 180 |
| | Comparative Example 3 | 200 | 130 | 80 | 35 | 10 |

Example 5

Figure 11:
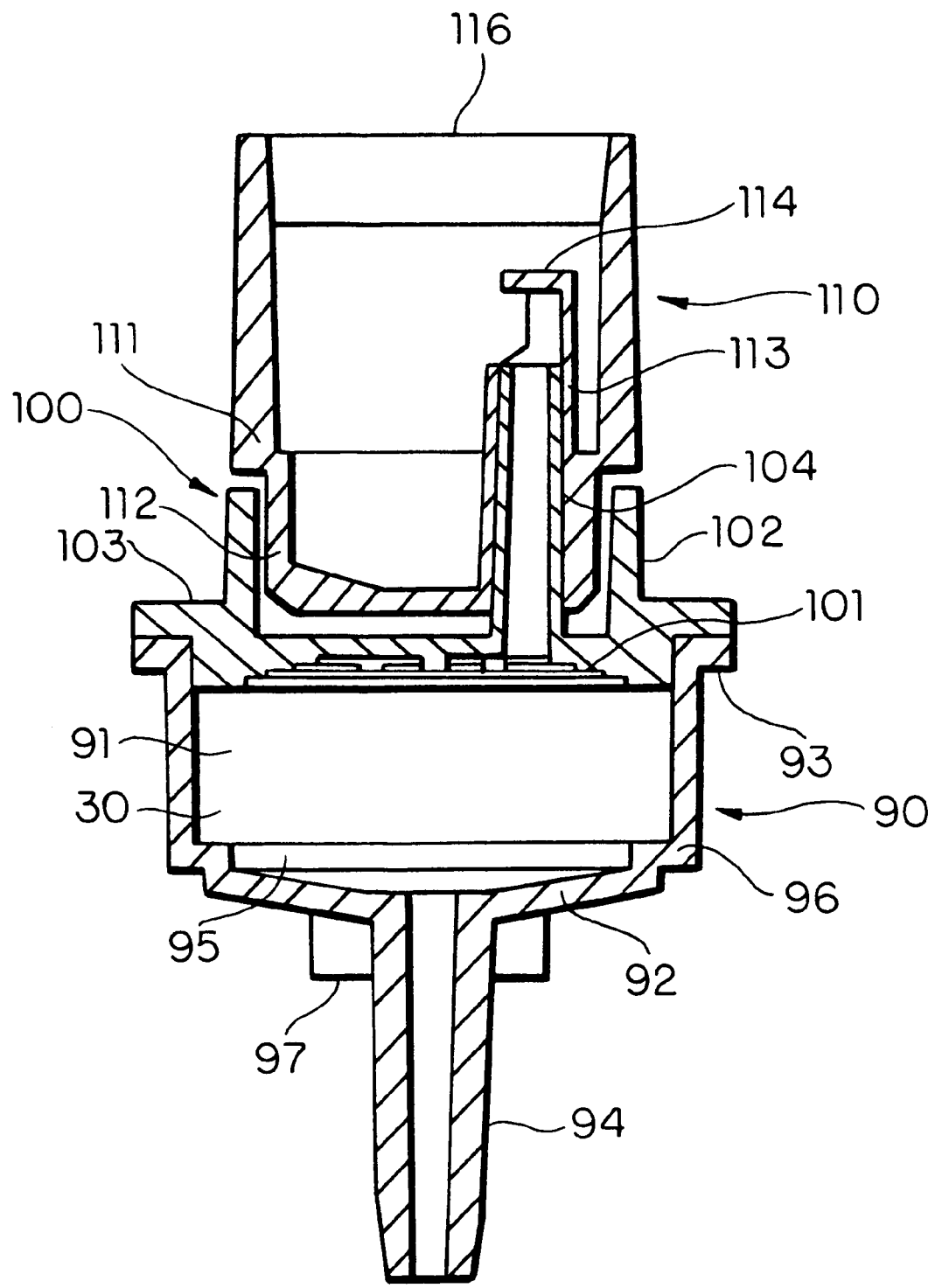
FIG. 11 is a longitudinal section of another blood filter unit embodiying the invention wherein a plasma receiver is separable.
Figure 12:
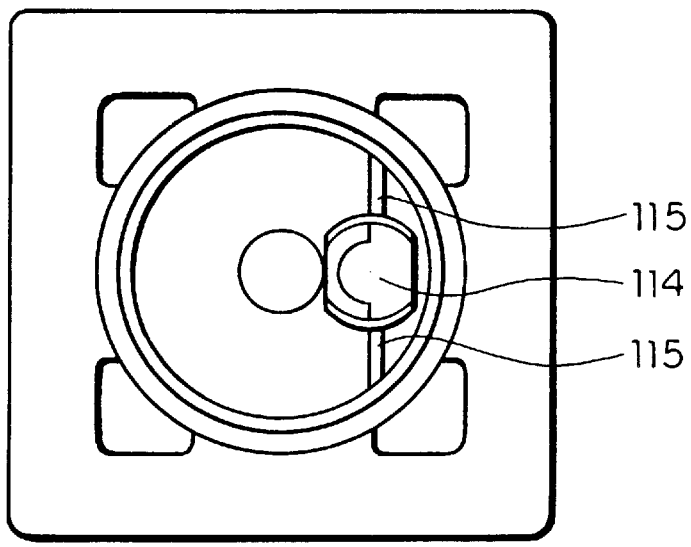
FIG. 12 is a plan view and FIG. 13 is a bottom view thereof.
Figure 13:
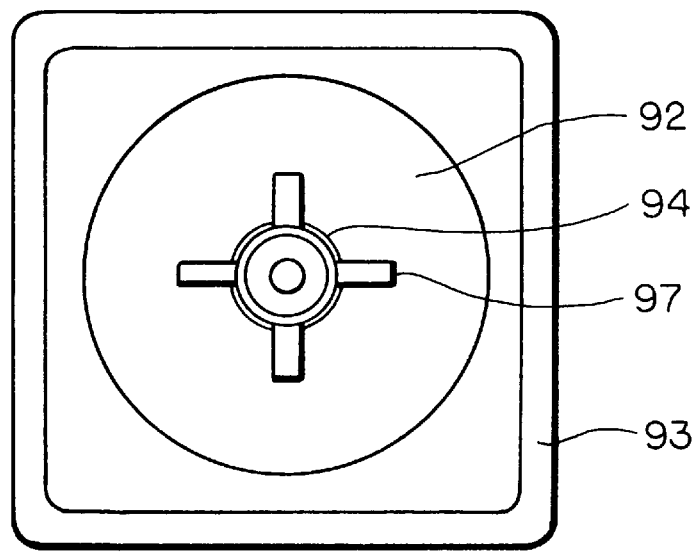

A blood filter unit illustrated in FIGS. 11–13 was prepared. The filter unit was in a plasma receiver-separable type, and was composed of a holder body 90, a cap 100 and a plasma receiver 110, as shown in FIG. 11 which illustrates an assembled state of the filter unit.

The holder body 90 is the same as the blood filter of Example 2.

The cap 100 and the plasma receiver 110 are similar to the cap 50 of Example 2 except that the plasma receiver is separated. That is, in the upper part of the cap 100, the plasma passage 104 is in a form of a smokestack without shaving, and a fitting wall 102 is formed in a form of short cylinder coaxial with the cap 100.

The plasma receiver 110 has almost the same outer diameter as the fitting wall 102. A step portion 111 is provided at the lower part, and a bottom portion 112 which is fitted to the fitting wall 102 is formed thereunder. The outer diameter of the bottom portion 112 is slightly smaller than the inner diameter of the fitting wall 102 so as to fit thereinto. A sheath 123, which is fitted to the plasma passage 104, is formed at the position of the bottom portion 112 corresponding to the plasma passage 104. The sheath 123 has a form of smokestack with shaving in parallel, and a pent-roof 114 is provided similar to Example 2.

Example 6

Figure 14:
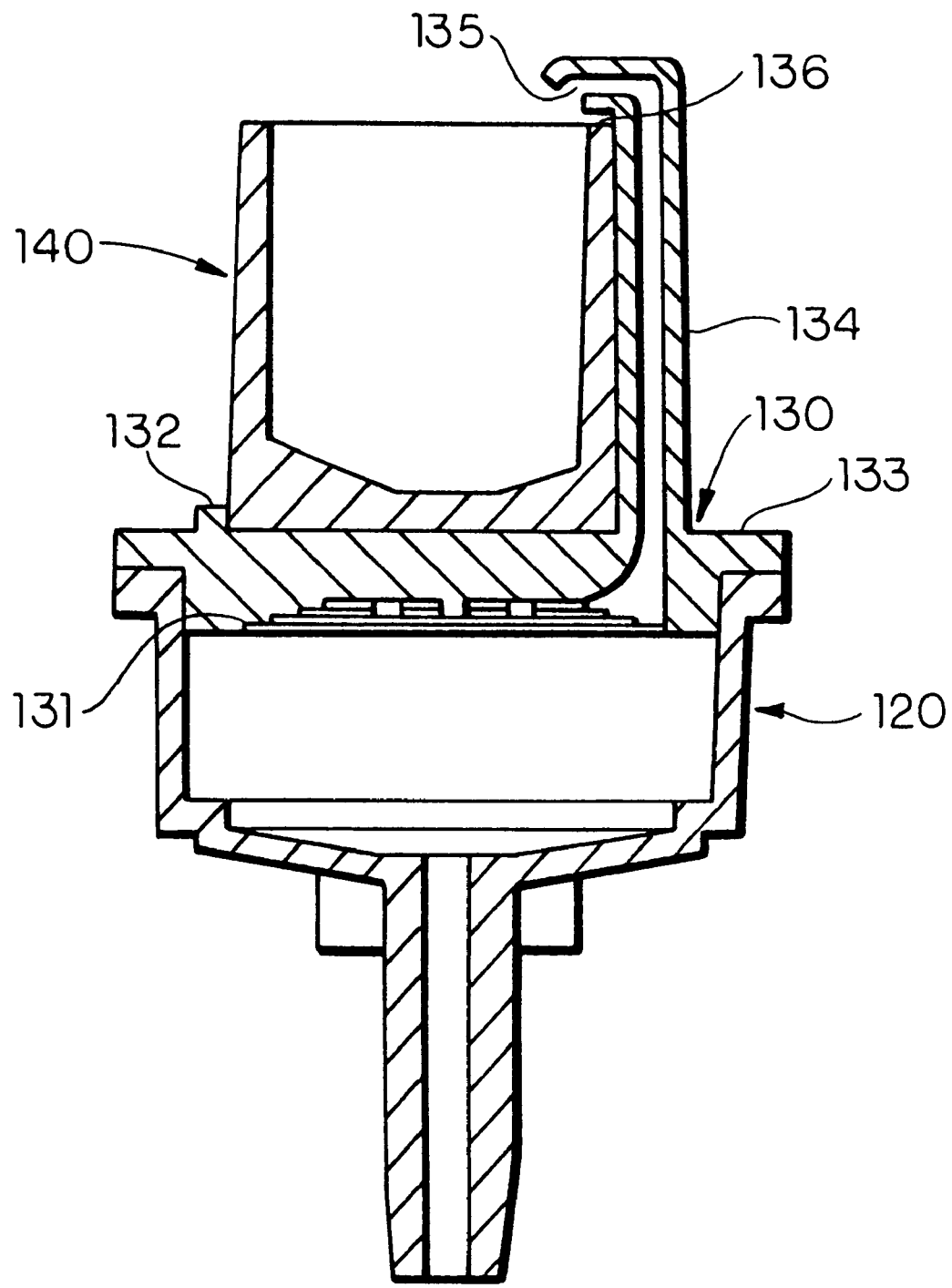
FIG. 14 is a longitudinal section of another blood filter unit embodying the invention wherein a plasma receiver is also separable.
Figure 15:
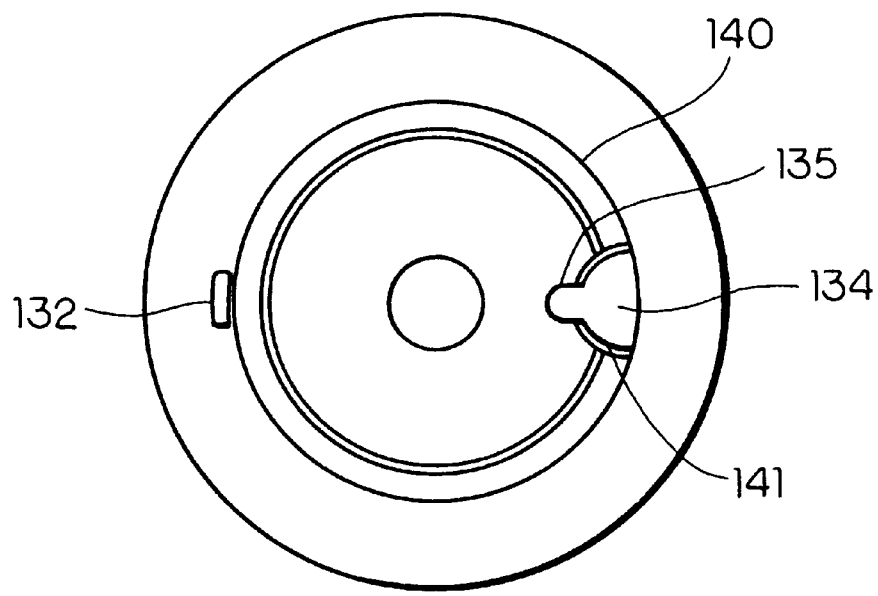
FIG. 15 is a plan view and FIG. 16 is a bottom view thereof.
Figure 16:
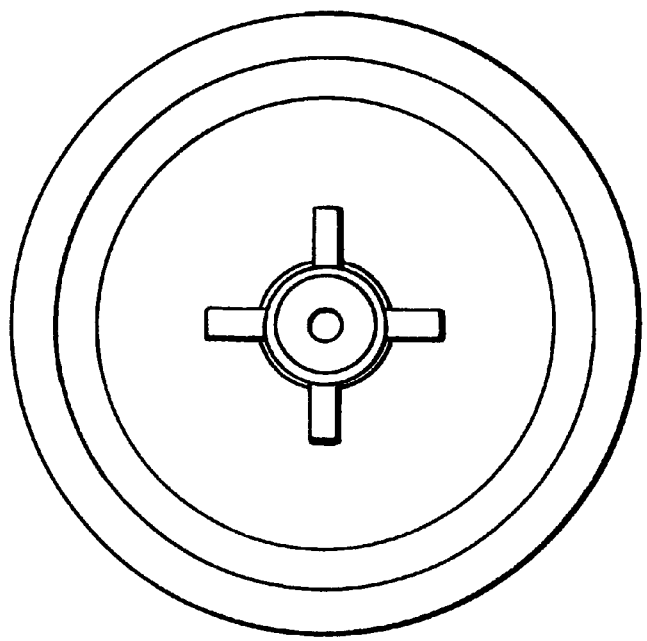

A blood filter unit illustrated in FIGS. 14–16 was prepared. The filter unit was in a plasma receiver-separable type, and was composed of a holder body 120, a cap 130 and a plasma receiver 140, as shown in FIG. 14 which illustrates an assembled state of the filter unit.

The holder body 120 is the same as the blood filter of Example 2. The cap 130 and the plasma receiver 140 are similar to the cap 50 of Example 2 except that the plasma receiver is separated. That is, in the upper part of the cap 130, the plasma passage 134 stands from the periphery of the space formed by steps 131, and the outer shape in section is, as shown in FIG. 15, a combination of a small half circle on the side facing the center of the cap 130 and an arc compensating the lacking part of the cylindrical plasma receiver 140. The upper end of the plasma passage 134 is bent toward inside, and a plasma discharge port 135 is formed on the underside of the upper end. The top face of the cap 130 is flat, and an engaging projection 132 for engaging the plasma receiver 140 is formed on the side opposite to the plasma passage 134.

The plasma receiver 140 is cylindrical, and a longitudinal channel 141 having a half circle section is formed for receiving the plasma passage 134. The height of the plasma receiver 140 is almost the same as the jaw portion 136 of the plasma passage 134. An engaging recess 142 is formed on the lower end of the outer periphery of the plasma receiver 140 at the position corresponding to the engaging projection 132.

When the plasma receiver 140 is attached to the cap 130, the plasma receiver 140 is enforced on the plasma passage 134 by the engaging projection 132, and the upward movement is restrained by the jaw portion 136 of the plasma passage 134. Thus, the plasma receiver 140 is fixed to the cap 130. When the plasma receiver 140 is detached, the receiver 140 is slightly turned upward on the engaging part with the jaw portion 136 as the axis.

Example 7

A blood filter unit shown in FIGS. 1–6 was used, and a suction tip 150 is attached to the blood inlet 24.

Figure 17:
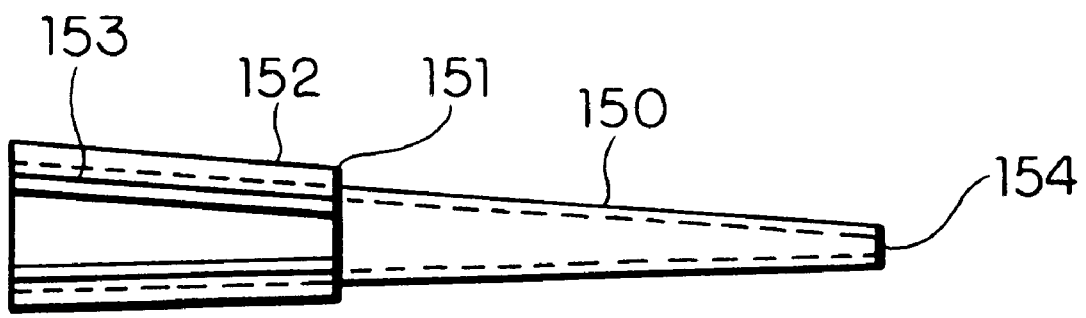
FIG. 17 is a side view of a suction tip attached to the blood inlet.
Figure 18:
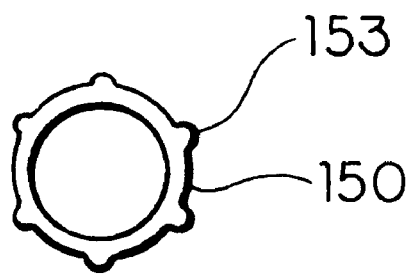
FIG. 18 is a plan view thereof.
Figure 19:
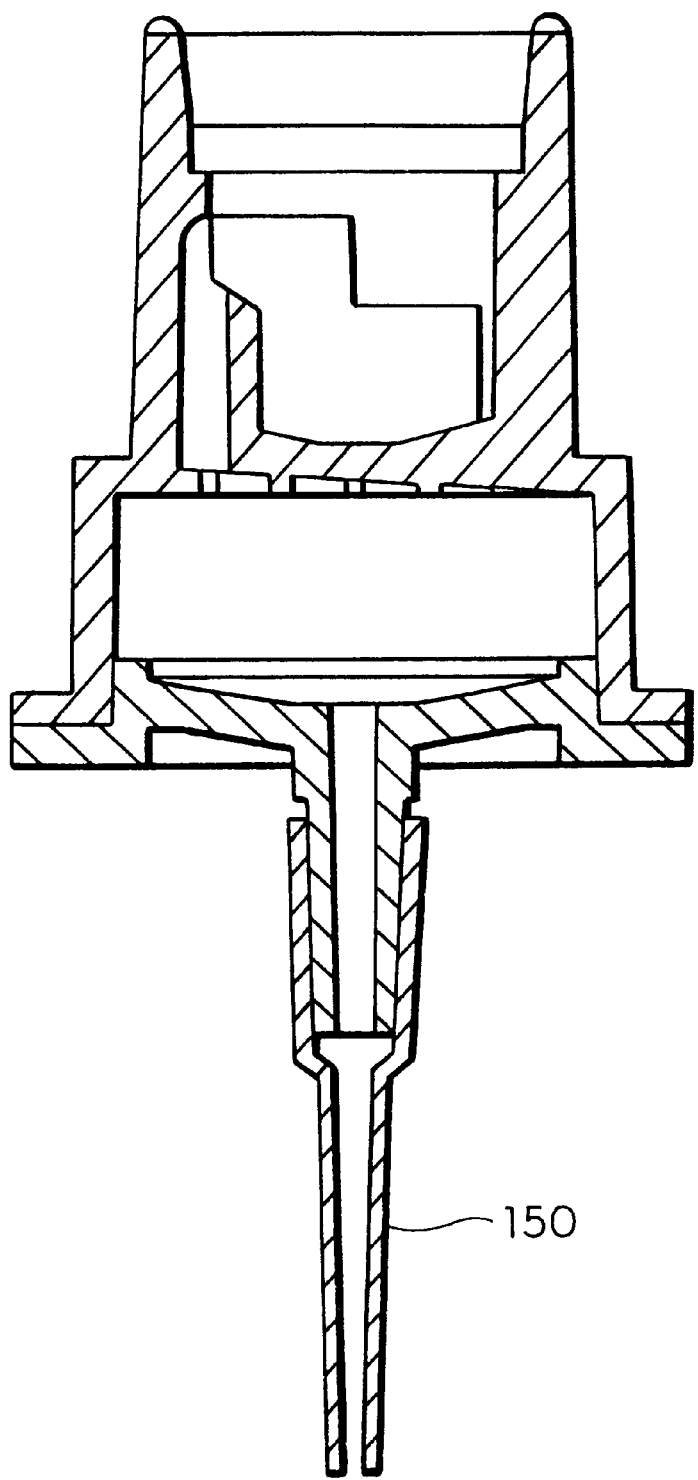
FIG. 19 is a longitudinal section of a blood filter unit to which the suction tip is attached.

The suction tip 150 is, as shown in FIGS. 17–18, in a form of a long truncated cone cylinder provided with a step portion 151 to narrow the diameter. Six longitudinal ribs 153 are formed on a large diameter portion 152. The opening at the narrowed end of the suction tip 150 is a suction port 154. The blood filter unit to which the suction tip is attached is shown in FIG. 19.

5 μl of heparin (0.1 unit) was placed in the plasma receiver 12.

Vein blood was drawn from healthy me and about 3 ml of the blood was pipetted into a sample tube not containing anticoagulant. After 15 minutes from drawing blood, the blood was filtered using the above filter unit to which the suction tip had been attached.

As a result, about 320 μl of serum was separated from 2 ml of the blood having a hematocrit value of 42%. The serum was left at room temperature overnight. The serum still kept fluidity, and deposition of fibrin was not observed.

Example 8

In Example 7, 0.1 unit plasmin was substituted for the heparin, a similar experiment was conducted. The serum obtained was left one day. Coagulation and deposition of fibrin were not observed.

Comparative Example 1

Using the same blood filter unit as Example 7 except that heparin was not added, the blood was filtered with suction under the same conditions as Example 7. As a result, about 310 μl of plasma was separated, and accumulated in the plasma receiver. After leaving the plasma for 30 minutes at room temperature, the plasma was observed. As a result, coagulation proceeded in the plasma, and fluidity was lost. The plasma was further left for 1 hour. Then, deposition of fibrin was observed, and coagulation further proceeded.

Example 9

The same blood filter unit as Example 7 was used. Instead of putting heparin in the plasma receiver, 5 μl (0.1 unit) of heparin was impregnated in the glass fiber filter located at the farthest position from the blood inlet, and then dried.

Using the blood filter unit, the blood was filtered under the same conditions as Example 7, and about 350 μl of plasma with good quality was obtained. The plasma was left one day, but fibrin was not deposited.

Example 10

Using the same blood filter unit as Example 7, 5 μl of heparin was applied to the plasma receiver and dried. Experiments were conducted similar to Example 7, and similar results were obtained.

Example 11

The same blood filter unit as Example 7 was used. Instead of putting heparin in the plasma receiver, 10 μl/cm$^2$ of heparin was impregnated in the polysulfone membrane, and then dried.

Using the blood filter unit, the blood was filtered under the same conditions as Example 7, and plasma without the occurrence of coagulation and deposition of fibrin was obtained similar to Example 7.

Example 12

10 ml of vein blood was drawn from a healthy man using a vacuum blood drawing tube 10 mm ø in inside diameter (Terumo) containing none of anticoagulant, coagulation accelerator, and separation accelerator, and each 2.5 ml was pipetted into plain sample tubes 7 mm in inside diameter. After leaving 5 hours, the blood was filtered using the same blood filter unit as Example 9 to which the suction tip an agglomerate checking member shown in FIGS. 20–21 had been attached. The agglomerate checking member was made of plastic, and had an outer diameter of 8 mm and an inner diameter of 6 mm. The grid was cross-shaped, and the thickness was 1 mm. As a result, blood agglomerates were stayed by the aggromerate checking member, and filtration proceeded smoothly.

Comparative Example 2

The blood was filtered with suction in the same manner as Example 12 except that the agglomerate checking member was not attached. As a result, the suction tip was clogged with blood agglomerates after 1–2 seconds from the start of filtration, and filtration could not be further carried out.

Example 13

An agglomerate checking member as shown in FIG. 23 was used. A polyethylene net having a mesh size of 0.5 mm×0.5 mm was punched into a disc 9.5 mm in diameter, and attached to the bottom of the truncated cone cylinder. Good filtration similar to Example 12 was obtained.

Example 14

An agglomerate checking member as shown in FIG. 22 was used. A net having a mesh size of 1 mm×1 mm was attached between the ring plate and disc. Good filtration similar to Example 13 was obtained.

I claim:

1. A blood filter unit which comprises a blood filtering material comprising a glass fiber filter and microporous membrane, a holder comprising a filter chamber, a filtrate receiver, a filtrate passage leading from the filter chamber to the filtrate receiver and a baffle at an exit of the filtrate passage, said filter chamber having a volume of 101 to 300% of the blood filtering material in the dry state and having a blood inlet located on an underside of the filter chamber and filtrate outlet located on an upside of the filter chamber, said filter chamber accommodating the blood filtering material so that the microporous membrane is located on the filtrate outlet side, and being provided with a space between the blood filtering material and the filtrate outlet, and having means for preventing adhesion of the blood filtering material on the filtrate outlet side, said filtrate receiver being located on the upside of the filter chamber.

2. The blood filter unit of claim 1 wherein said means for preventing adhesion is a solid material arranged so as to leave liquid passages.

3. The blood filter unit of claim 2 wherein the contact area of the solid material with the blood filtering material is 1 to 10% of effective filtering area upon filtering.

4. The blood filter unit of claim 2 wherein said solid material is composed of projections or a spacer.

5. The blood filter unit of claim 1 which further comprises a space capable of contacting blood over the entire surface of the blood filtering material provided between the blood filtering material and the blood inlet.

6. The blood filter unit of claim 1 which further comprises a plasma receiver, separable from the filter unit.

7. The blood filter unit of claim 1 wherein the blood filtering material is closely fitted in the filter chamber to avoid blood bypassing the filtering material.

8. The blood filter unit of claim 1 wherein the filtrate passage is formed at a periphery of the filtrate receiver.

* * * * *